United States Patent
Lohrmann et al.

(10) Patent No.: US 9,820,489 B2
(45) Date of Patent: Nov. 21, 2017

(54) ENHANCEMENT OF THE SPORICIDAL EFFICACY OF ALCOHOL AND PEROXIDE COMPOSITIONS

(71) Applicant: ECOLAB USA INC., St. Paul, MN (US)

(72) Inventors: Elke Lohrmann, Cologne (DE); Stefan Jaeger, Cologne (DE); Laurence Geret, Pulheim (DE); Bernhard Meyer, Mettmann (DE)

(73) Assignee: Ecolab USA Inc., Saint Paul, MN (US)

( * ) Notice: Subject to any disclaimer, the term of this patent is extended or adjusted under 35 U.S.C. 154(b) by 51 days.

(21) Appl. No.: 14/654,260

(22) PCT Filed: Dec. 21, 2012

(86) PCT No.: PCT/EP2012/076809
§ 371 (c)(1),
(2) Date: Jun. 19, 2015

(87) PCT Pub. No.: WO2014/094911
PCT Pub. Date: Jun. 26, 2014

(65) Prior Publication Data
US 2015/0327555 A1 Nov. 19, 2015

(51) Int. Cl.

| | | |
|---|---|---|
| *A01N 59/00* | (2006.01) | |
| *A01N 31/02* | (2006.01) | |
| *A61L 2/18* | (2006.01) | |
| *C11D 3/18* | (2006.01) | |
| *C11D 3/20* | (2006.01) | |
| *C11D 3/39* | (2006.01) | |
| *C11D 3/395* | (2006.01) | |
| *C11D 3/43* | (2006.01) | |
| *C11D 3/48* | (2006.01) | |
| *C11D 7/24* | (2006.01) | |
| *C11D 7/26* | (2006.01) | |
| *C11D 7/50* | (2006.01) | |

(52) U.S. Cl.
CPC .............. *A01N 59/00* (2013.01); *A01N 31/02* (2013.01); *A61L 2/186* (2013.01); *C11D 3/18* (2013.01); *C11D 3/181* (2013.01); *C11D 3/2006* (2013.01); *C11D 3/3947* (2013.01); *C11D 3/3956* (2013.01); *C11D 3/43* (2013.01); *C11D 3/48* (2013.01); *C11D 7/24* (2013.01); *C11D 7/241* (2013.01); *C11D 7/261* (2013.01); *C11D 7/5022* (2013.01)

(58) Field of Classification Search
CPC .......... A61L 2/186; C11D 3/18; C11D 3/181; C11D 3/2006; C11D 3/3947; C11D 3/3956; C11D 3/48; C11D 7/24; C11D 7/241; C11D 7/261; C11D 7/5022; C11D 3/43; A01N 31/02; A01N 59/00
See application file for complete search history.

(56) References Cited

U.S. PATENT DOCUMENTS

| | | | | |
|---|---|---|---|---|
| 4,536,313 A | * | 8/1985 | Hignett | C07C 409/42 252/186.42 |
| 6,316,399 B1 | | 11/2001 | Melikyan et al. | |
| 2004/0213750 A1 | * | 10/2004 | Bennett | A01N 31/02 424/70.1 |
| 2009/0324508 A1 | * | 12/2009 | Bobbert | A01N 31/02 424/45 |
| 2010/0055198 A1 | * | 3/2010 | Wang | A01N 31/02 424/616 |

FOREIGN PATENT DOCUMENTS

| | | |
|---|---|---|
| DE | 4431577 A1 | 3/1996 |
| DE | 102009001973 A1 | 10/2010 |
| JP | 5378985 A | 7/1978 |
| WO | 2008094718 A1 | 8/2008 |

OTHER PUBLICATIONS

PubChem—"Pentane." Retrieved May 1, 2016. Retrieved from the internet <URL: https://pubchem.ncbi.nlm.nih.gov/compound/pentane#section=Top>, pp. 1-71.*
ECOLAB USA Inc. "International Search Report" PCT/EP2012/076809, dated Sep. 20, 2013, 4 pages Sep. 20, 2013.

* cited by examiner

*Primary Examiner* — Anoop Singh
*Assistant Examiner* — Doan Phan
(74) *Attorney, Agent, or Firm* — McKee, Voorhees & Sease, PLC

(57) ABSTRACT

The present invention relates to a liquid composition comprising: a) at least one alcohol; b) at least one hydrocarbon or hydrocarbon mixture; c) at least one peroxide agent; d) water. The compositions of the invention possess antimicrobial and enhanced sporicidal properties.

16 Claims, No Drawings

US 9,820,489 B2

ENHANCEMENT OF THE SPORICIDAL EFFICACY OF ALCOHOL AND PEROXIDE COMPOSITIONS

CROSS REFERENCE TO RELATED APPLICATION

This is a national stage application of International Application No. PCT/EP2012/076809, filed Dec. 21, 2012, published as PCT Publication WO 2014/094911 Al on Jun. 26, 2014, the entire disclosure of which is incorporated herein by reference in its entirety.

FIELD OF THE INVENTION

The present invention relates to peroxide and alcohol containing compositions with enhanced antimicrobial and sporicidal activity, compositions, and methods of making and using these compounds.

Peroxide agents are widely known for use as antimicrobials and bleaching agents. However, peroxides have a tendency to decompose and have limited storage stability. Further, the concentration of peroxides, such as hydrogen peroxide, may become critical to handle if it is used at sporicidal concentrations. Also, most peroxycarboxylic acids have an unpleasant odor and limited water solubility.

Alcohol, especially ethanol and propanol, are widely known for use as antimicrobials with a fast kill of vegetative bacteria and yeasts. However, these substances do not provide a sporicidal effect at applicable contact times.

Thus, a need exists for low or no odor, water soluble peroxy containing compounds and compositions that also possess antimicrobial and enhanced sporicidal properties.

SUMMARY

In some aspects, the present invention relates to peroxide and alcohol containing compositions with antimicrobial and enhanced sporicidal activity, compositions, and methods of making and using these compounds.

The compositions of the invention possess antimicrobial and enhanced sporicidal properties.

In some embodiments the compositions have low or no-odor.

In some embodiments the composition compensates slow sporicidal effect of low peroxide concentration in alcohol solution due to the enhanced sporicidal activity.

In some aspects, the present invention can be used to reduce and/or to kill microorganisms, in particular bacterial endospores.

In some aspects, the present invention provides methods for using the compounds of the present invention as antimicrobial, microbicidal and/or sporicidal agents.

The compositions of the present invention may have many uses including, but not limited to disinfection, antimicrobial, sporicidal, bleaching and/or cleaning agents.

DETAILED DESCRIPTION

The present invention relates to a liquid composition comprising:
at least one alcohol;
at least one hydrocarbon or hydrocarbon mixture;
at least one peroxide agent;
water.

According to one embodiment of the liquid composition the weight ratio of at least one alcohol, preferably a $C_2$ to $C_6$-alcohol, to the at least one hydrocarbon or hydrocarbon mixture is in the range of about 5:1 to 100:0.1, preferably in the range of about 25:1 to 100:0.1 and more preferred in the range of about 40:1 to 100:0.1.

In some embodiments all components of the liquid composition are liquid at 23° C.

In some embodiments the liquid composition is adjusted to a pH in the range of about ≥1.0 to about ≤10.0, preferably in the range of about ≥2.0 to about ≤8.0, further preferred in the range of about ≥2.5 to about ≤6.0.

The pH can be adjusted by addition of organic and/or inorganic acids. Further, the pH can be adjusted by addition of alkaline substances. It is also possible to add a buffer solution to stabilize a desired pH value.

In some embodiments the alcohol is selected from the group comprising ethanol, 1-propanol, 2-propanol, 1-butanol, 2-butanol and/or tert-butanol, preferably ethanol, 1-propanol and/or 2-propanol and more preferred 1-propanol and/or 2-propanol.

In some embodiments the hydrocarbon or hydrocarbon mixture being liquid at 23° C. is selected from the group comprising a petroleum ether and/or a $C_5$ to $C_{12}$ saturated and/or unsaturated, linear and/or cyclic hydrocarbon.

In some embodiments the peroxide agent is selected from the group comprising $H_2O_2$ and/or at least one peroxycarboxylic acid. However in some embodiments, the more preferred peroxide agent is $H_2O_2$.

In some embodiments, the compositions of the present invention comprise at least one carboxylic and/or percarboxylic acid.

In some embodiments, the compositions of the present invention comprise at least two, at least three, or at least four or more carboxylic and/or percarboxylic acids.

In some embodiments the peroxycarboxylic acid is a $C_2$ to $C_{18}$ peroxycarboxylic acid, further preferred a $C_2$ to $C_4$ peroxycarboxylic acid and/or $C_5$ to $C_8$ peroxycarboxylic acid.

In some embodiments the peroxycarboxylic acid is a peroxyacetic acid and/or peroxyoctanoic acid.

In some embodiments, the compositions of the present invention is free of a carboxylic and/or percarboxylic acid.

In some embodiments the composition is free of a phosphorus component.

In some embodiments the composition may comprises additional functional ingredients, for example, acid, chelant, buffer, hydrotrope, phosphorus and/or tenside.

In some embodiments the composition is free of additional functional ingredients selected from the group of acid, chelant, buffer, hydrotrope, phosphorus component and/or tenside.

Definitions

So that the invention maybe more readily understood, certain terms are first defined.

As used herein, "weight percent", "wt-%", "percent by weight", "% by weight" and variations thereof refer to the concentration of a substance as the weight of that substance divided by the total weight of the composition and multiplied by 100.

It is understood that all the components of the composition of the invention are selected such that they are in total 100 wt.-%.

It is understood that, as used here, "percent", "%", and the like are intended to be synonymous with "weight percent", "wt-%", etc.

It is understood that all temperatures, as used in this specification and the appended claims, are based on a normal atmospheric pressure of 1013.25 mbar (=1013.25 hPa), unless the content clearly dictates otherwise.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims comprise equivalents to the quantities.

It should be noted that, as used in this specification and the appended claims, the singular forms "a", "an", and "the" comprise plural referents unless the content clearly dictates otherwise.

Thus, for example, reference to a composition containing "a compound" comprises a composition having two or more compounds.

It should also be noted that the term "or" is generally employed in its sense including "and/or" unless the content clearly dictates otherwise.

As used herein, the term "microorganism", refers to any noncellular or unicellular, comprising colonial, organism. Microorganisms comprise all prokaryotes. Microorganisms comprise bacteria, comprising cyanobacteria, spores, lichens, fungi, protozoa, virinos, viroids, viruses, phages, and some algae.

As used herein, the term "phosphorus-free" or "substantially phosphorus-free" component refers to a composition, mixture, or ingredient that does not contain phosphorus or a phosphorus-containing compound or to which phosphorus or a phosphorus-containing compound has not been added.

As used herein, the phrase "food processing surface" refers to a surface of a tool, a machine, equipment, a structure, a building, or the like that is employed as part of a food processing, preparation, or storage activity.

Examples of food processing surfaces comprise surfaces of food processing or preparation equipment, e.g. slicing, canning, or transport equipment, including flumes, of food processing wares, e.g. utensils, dishware, wash ware, and bar glasses, and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the term "ware" refers to items such as eating and cooking utensils, dishes, and other hard surfaces such as showers, sinks, toilets, bathtubs, countertops, windows, mirrors, transportation vehicles, and floors.

As used herein, the term "ware washing" refers to washing, cleaning, or rinsing ware. Ware also refers to items made of plastic. Types of plastics that can be cleaned with the compositions according to the invention comprise but are not limited to, those that comprise polycarbonate polymers (PC), acrilonitrile-butadiene-styrene polymers (ABS), and polysulfone polymers (PS). Another exemplary plastic that can be cleaned using the compounds and compositions of the invention comprise polyethylene terephthalate (PET).

As used herein, the phrase "air streams" comprise food anti-spoilage air circulation systems. Air streams also comprise air streams typically encountered in hospital, surgical, infirmity, birthing, mortuary, and clinical diagnosis rooms.

As used herein, the phrase "health care surface" refers to a surface of an instrument, a device, a cart, a cage, furniture, a structure, a building, or the like that is employed as part of a health care activity. Examples of health care surfaces comprise surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces", such as walls, floors, bed-pans, etc., or fabric surfaces, e.g. knit, woven, and non-woven surfaces, such as surgical garments, draperies, bed linens, bandages, etc., or patient-care equipment, such as respirators, diagnostic equipment, shunts, body scopes, wheel chairs, beds, etc., or surgical and diagnostic equipment. Health care surfaces comprise articles and surfaces employed in animal health care. Health care surfaces can be of all types of materials, such as metals, plastics, wood, coatings and there like.

As used herein, the term "instrument" refers to the various medical or dental instruments or devices that can benefit from cleaning with a composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment comprise, but are not limited to: diagnostic instruments, trays, pans, holders, racks, forceps, scissors, shears, saws, e.g. bone saws and their blades, hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes, e.g., endoscopes, stethoscopes, and arthoscopes and related equipment, and the like, or combinations thereof.

As used herein, "agricultural" or "veterinary" objects or surfaces comprise animal feeds, animal watering stations and enclosures, animal quarters, animal veterinarian clinics, e.g. surgical or treatment areas, animal surgical areas, and the like.

The composition of the present invention can be used to treat surfaces, such as for microbial reduction on surfaces of pharmacies, of pharmaceutical equipment and/or parts thereof, especially for equipment in those settings.

As used herein, the phrase "pharmaceutical equipment" includes pharmaceutical machinery and medical products that are meant to be used in manufacturing and processing of pharmaceuticals and drugs. Further, "pharmaceutical equipment" comprises pharmaceutical processing equipment for tabletting, powder processing, capsulation as well as R&D equipment and instrumentation, material handling, coating, bulk drug plant installation, packaging machinery etc. Under the broader category of pharmaceutical equipment are also included pharmaceutical processing equipment, pharmaceutical packaging equipment, pharmaceutical filling equipment, pharmaceutical sterilizers, pharmaceutical sealing machines, pharmaceutical labeling machines, pharmaceutical vessels, pharmaceutical mixers, pharmaceutical washing machines, pharmaceutical coating machines, pharmaceutical granulators, pharmaceutical inspection machines, pharmaceutical laboratory equipment, analytical instruments, scientific instruments, medical device for research as well as validation equipment.

For the purpose of this patent application, successful microbial reduction is achieved when the microbial populations are reduced by at least about ≥99.9%, if these are bacterial endospores, 99.99%, if these are fungi or viruses and 99.999%, if these are vegetative bacteria As used herein, the term "sanitizer" refers to an agent that reduces the number of bacterial contaminants to safe levels as judged by public health requirements.

In an embodiment, sanitizers for use in this invention will provide at least a 99.9% reduction of bacterial spores that corresponds to a 3-log order reduction. Depending on the efficacy spectrum reductions can be evaluated using procedures set out in European Standards like EN 13704 (sporicidal), EN 1276/EN13727 (bactericidal), EN 1650/13624 (fungicidal), EN 14476 (virucidal) and EN 13697 (bactericidal, fungicidal) or other relevant standards for the above mentioned application areas.

As used herein, the term "disinfectant" refers to an agent that kills all vegetative cells including most recognized pathogenic microorganisms, using the procedure described in A. O. A. C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term 'intermediate-level disinfection' or 'intermediate level disinfectant' refers to a compound or composition that kills mycobacteria, most viruses, and bacteria with a chemical germicide registered as a tuberculocide by the Environmental Protection Agency (EPA).

As used herein, the term "low-level disinfection" or "low level disinfectant" refers to a compound or composition that kills some viruses and bacteria with a chemical germicide registered as a hospital disinfectant by the EPA.

As used in this invention, the term "sporicidal" refers to a physical or chemical agent or process having the ability to cause greater than a 99.9% reduction (3-log order reduction) in the population of spores of *Bacillus cereus* or *Bacillus subtilis* within a defined contact time. Differentiation of antimicrobial "-cidal" or "-static" activity, the definitions which describe the degree of efficacy, and the official laboratory protocols for measuring this efficacy are considerations for understanding the relevance of antimicrobial agents and compositions.

Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic.

A sanitizer and a disinfectant are, by definition, agents which provide antimicrobial or microbiocidal activity. In contrast, a preservative is generally described as an inhibitor or microbistatic composition.

Compounds of the Invention

The present invention relates, at least in part, to a liquid composition comprising at least one alcohol, at least one hydrocarbon or hydrocarbon mixture, at least one peroxide agent as well as water, and the use thereof in a variety of bleaching, disinfecting and cleaning applications, in particular the use as a sporicidal agent.

Additional ingredients suitable for use with the compositions of the present invention comprise, but are not limited to, carboxylic acids, surfactants, stabilizing agents, e.g., metal chelators, and mixtures thereof.

Alcohol

The liquid composition of the present invention comprises at least one alcohol. Examples of suitable alcohols are selected from the group of, but are not limited to, ethanol, 1-propanol, 2-propanol, n-butan-1-ol, n-butan-2-ol, tert-butanol, and/or pentan-1-ol, pentan-2-ol, pentan-3-ol, 3-methylbutan-2-ol, and/or 2,2-dimethylpropanol, hexan-1-ol, hexan-2-ol, hexan-3-ol and/or isomers thereof as well as mixtures thereof.

In some embodiments the alcohol that is preferred is ethanol and/or propanol, further preferred is 1-propanol and/or 2-propanol, but more preferred is 1-propanol.

In some embodiments, the liquid compositions of the present invention comprise about ≥10 wt.-% to about ≤95 wt.-%, preferably about ≥30 wt.-% to about ≤90 wt.-%, further preferred about ≥40 wt.-% to about ≤80 wt.-%, of an alcohol, preferably ethanol and/or propanol, further preferred is 1-propanol and/or 2-propanol, and more preferred is 1-propanol.

Hydrocarbon

The liquid composition of the present invention comprises at least one hydrocarbon. Hydrocarbons useful in the compositions and methods of the present invention are hydrocarbons or hydrocarbon mixtures that are liquid at 23° C.

In some embodiments suitable hydrocarbons for use are selected from the group of, but are not limited to, petroleum ether and/or a $C_5$ to $C_{12}$ saturated and/or unsaturated, linear and/or cyclic hydrocarbon.

Petroleum ether is a group of various volatile, highly flammable, liquid hydrocarbon mixtures used chiefly as nonpolar solvents. Petroleum ether, also referred herein as "petroleum ether fraction", is obtainable from petroleum refineries as the portion of the distillate which is intermediate between the lighter naphtha and the heavier kerosene. Petroleum ethers that can be used have a specific gravity of between 0.6 and 0.8 depending on its composition. The following distillation fractions of petroleum ether, useful in the compositions and methods of the present invention, having a boiling point in the range of about ≥30° C. to about ≤40° C., of about ≥40° C. to about ≤60° C., of about ≥60° C. to about ≤80° C., of about ≥80° C. to about ≤100° C., of about ≥80° C. to about ≤120° C. and sometimes of about ≥100° C. to about ≤120° C.

Petroleum ether useful in the compositions and methods of the present invention comprises a mixture of alkanes, for example a mixture of pentane, hexane, and/or heptanes.

In some embodiments of the liquid compositions a petroleum ether, also referred to as petroleum ether fraction, having a boiling point in the range of about ≥60° C. to about ≤80° C. or about ≥40° C. to about ≤60° C. can be used.

In some embodiments, the liquid compositions of the present invention comprise about ≥0.1 wt.-% to about ≤10 wt.-%, preferably about ≥0.5 wt.-% to about ≤5 wt.-%, further preferred about ≥0.5 wt.-% to about ≤3 wt.-%, of a hydrocarbon or hydrocarbon mixture, preferably a hydrocarbon or hydrocarbon mixture that is liquid at 23° C.

In some embodiments, the liquid compositions of the present invention comprise about ≥0.1 wt.-% to about ≤10 wt.-%, preferably about ≥0.5 wt.-% to about ≤5 wt.-%, further preferred about ≥0.5 wt.-% to about ≤3 wt.-%, of a hydrocarbon or hydrocarbon mixture, preferably a hydrocarbon or hydrocarbon mixture having a boiling point in the range of about ≥40° C. to about ≤80° C. and more preferred of about ≥40° C. to about ≤60° C.

Peroxide Agent

In some embodiments, the compositions of the present invention comprise at least one peroxide agent. As used herein, the term "peroxide agent" refers to any composition capable of generating oxygen gas in situ on and in a soil, as well as in solution. In some embodiments, the active oxygen source is a compound capable of providing oxygen gas in situ on and in the soil upon contact with an activator complex, such as an iron(III) activator complex. The compound may be organic, or inorganic.

Exemplary peroxide agents for use in composition and methods of the present invention comprise, but are not limited to, peroxygen compounds, hydrogen peroxide, chlorine dioxide, sulfur dioxide, peroxycarboxylic acid and derivatives thereof. In some embodiments, the peroxide agent does not comprise a chlorine containing group.

In some embodiments, the liquid compositions of the present invention comprise about ≥0.1 wt.-% to about ≤30 wt.-%, preferably about ≥0.5 wt.-% to about ≤20 wt.-%, further preferred about ≥1 wt.-% to about ≤10 wt.-%, of a peroxide agent, preferably hydrogen peroxide ($H_2O_2$) and/or a peroxycarboxylic acid and more preferred hydrogen peroxide.

Carboxylic Acids

The addition of at least one carboxylic acid may further improve the sporicidal activity of the liquid composition.

Examples of suitable carboxylic acids comprise, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof.

In some embodiments, the liquid compositions of the present invention comprise about ≥0.01 wt.-% to about ≤30 wt.-%, preferably about ≥0.01 wt.-% to about ≤10 wt.-%, further preferred about ≥0.01 wt.-% to about ≤5 wt.-%, of a carboxylic acid.

In some embodiments the pH can be adjusted by adding alkaline substances as e.g. monoethanolamine, diethanolamine, triethanolamine, other amines, NaOH or KOH.

Peroxycarboxylic Acids

The addition of at least one peroxycarboxylic acid may further improve the sporicidal activity of the liquid composition.

Examples of peroxycarboxylic acids useful in the compositions and methods of the present invention comprises peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, or the peroxyacids of their branched chain isomers, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof.

In some embodiments, the compositions of the invention utilize a combination of several different peroxycarboxylic acids.

In some embodiments, the liquid compositions of the present invention comprise about ≥0.1 wt.-% to about ≤5 wt.-%, preferably about ≥0.1 wt.-% to about ≤3 wt.-%, further preferred about ≥0.1 wt.-% to about ≤1 wt.-%, of a peroxycarboxylic acid.

In some embodiments, the compositions of the invention do not comprise a peroxycarboxylic acid.

Surfactants

In some embodiments, the liquid compositions of the present invention comprise at least one surfactant.

Surfactants suitable for use with the liquid compositions of the present invention comprise, but are not limited to, nonionic surfactants, anionic surfactants, and zwitterionic surfactants.

In some embodiments, the liquid compositions of the present invention comprise about ≥0.1 wt.-% to about ≤20 wt.-%, preferably about ≥0.1 wt.-% to about ≤10 wt.-%, further preferred about ≥0.1 wt.-% to about ≤5 wt.-%, of a surfactant.

In some embodiments, the compositions of the invention do not comprise an additional surfactant.

Water

The liquid compositions of the present invention comprise water. As used herein, the term "water" comprises inter alia distilled water, double distilled water, tape water having drinking water quality, and/or water having a water quality that is accepted for the desired use of the liquid composition of the present invention.

In some embodiments, the liquid compositions of the present invention comprise about ≥0 wt.-% to about ≤90 wt.-%, preferably about ≥0 wt.-% to about ≤70 wt.-%, further preferred about ≥0 wt.-% to about ≤60 wt.-%, of water.

Liquid Compositions

In some embodiments the liquid composition comprises:
at least one $C_2$ to $C_6$-alcohol;
at least one hydrocarbon or hydrocarbon mixture;
at least one peroxide agent;
water.

In some embodiments the liquid composition comprises:
at least one alcohol selected from the group comprising ethanol, 1-propanol and/or iso-propanol;
at least one hydrocarbon or hydrocarbon mixture, wherein the hydrocarbon or hydrocarbon mixture is liquid at 23° C.;
at least one peroxide agent; wherein the peroxide agent is selected from the group comprising hydrogen peroxide and/or at least one peroxycarboxylic acid;
water.

In some embodiments the liquid composition comprises:
about ≥10 wt.-% to about ≤90 wt.-% of at least one alcohol;
about ≥0.1 wt.-% to about ≤10 wt.-% of at least one hydrocarbon or hydrocarbon mixture;
about ≥0.1 wt.-% to about ≤30 wt.-% of at least one peroxide agent;
water add. to 100 wt.-%, wherein the components are selected such that the total amount of all components does not exceed 100 wt.-% and the wt.-% of the components are based on the total weight amount of the composition.

In some embodiments the liquid composition comprises:
about ≥0.1 wt.-% to about ≤10 wt.-%, preferably about ≥0.5 wt.-% to about ≤8 wt.-%, further preferred about ≥1 wt.-% to about ≤6 wt.-%, more preferred about ≥2 wt.-% to about ≤4 wt.-%, of at least one hydrocarbon, preferably a petrol ether, and more preferred a petrol ether that has a boiling point of about ≥40° C. to ≤60° C.

In some embodiments the liquid composition comprises: about ≥10 wt.-% to about ≤95 wt.-%, preferably about ≥30 wt.-% to about ≤90 wt.-%, further preferred about ≥40 wt.-% to about ≤80 wt.-%, and in addition preferred about ≥50 wt.-% to about ≤60 wt.-%, of at least one $C_2$ to $C_6$-alcohol, preferably ethanol or propanol, and more preferred 1-propanol.

In some embodiments the liquid composition comprises: about ≥0.1 wt.-% to about ≤30 wt.-%, preferably about ≥0.5 wt.-% to about ≤20 wt.-%, further preferred about ≥1 wt.-% to about ≤10 wt.-%, additional preferred ≥3 wt.-% to about ≤8 wt.-%, and also preferred ≥4 wt.-% to about ≤6 wt.-%, of at least one peroxide agent, preferably hydrogen peroxide.

In some embodiments the liquid composition comprises:
- about ≥30 wt.-% to about ≤90 wt.-% of at least one alcohol selected from the group comprising ethanol, 1-propanol and/or 2-propanol;
- about ≥0.1 wt.-% to about ≤5 wt.-% of at least one hydrocarbon or hydrocarbon mixture, wherein the hydrocarbon or hydrocarbon mixture is liquid at 23° C.;
- about ≥0.1 wt.-% to about ≤20 wt.-% of at least one peroxide agent; wherein the peroxide agent is selected from the group comprising hydrogen peroxide and/or at least one peroxycarboxylic acid;
- water add. to 100 wt.-%, wherein the components are selected such that the total amount of all components does not exceed 100 wt.-% and the wt.-% of the components are based on the total weight amount of the composition.

In some embodiments the liquid composition comprises:
- about ≥40 wt.-% to about ≤80 wt.-% of at least one ethanol, 1-propanol and/or 2-propanol;
- about ≥0.1 wt.-% to about ≤3 wt.-% of at least one hydrocarbon or hydrocarbon mixture having a boiling point in the range of about ≥40° C. to about ≤80° C. and more preferred of about ≥40° C. to about ≤60° C.;
- about ≥0.1 wt.-% to about ≤10 wt.-% of hydrogen peroxide and/or a peroxycarboxylic acid;
- water add. to 100 wt.-%, wherein the components are selected such that the total amount of all components does not exceed 100 wt.-% and the wt.-% of the components are based on the total weight amount of the composition.

In some embodiments the liquid composition comprises:
- about ≥40 wt.-% to about ≤80 wt.-% of at least a propanol;
- about ≥0.1 wt.-% to about ≤3 wt.-% of at least one hydrocarbon or hydrocarbon mixture having a boiling point in the range of about ≥40° C. to about ≤60° C.;
- about ≥0.1 wt.-% to about ≤10 wt.-% of hydrogen peroxide;
- water add. to 100 wt.-%, wherein the components are selected such that the total amount of all components does not exceed 100 wt.-% and the wt.-% of the components are based on the total weight amount of the composition.

Use Compositions

The liquid compositions of the present invention can be present in the form of a in the form of a ready to use composition.

The level of active components in the composition is dependent on the the desired activity of the liquid compositions that is applied to an object to be treated therewith.

Uses of the Liquid Composition

In some embodiments, the liquid compositions of the present invention can also be used as disinfectant or antimicrobial compositions.

In some embodiments, the liquid compositions of the present invention of the present invention can be used for various applications, e.g., food contact sanitizing, hard surface disinfection, textile disinfection and disinfection of human skin.

In some embodiments, the liquid compositions of the present invention can be used as a sanitizing composition for articles cleaned using a clean in place (CIP) technique.

In other embodiments, the liquid compositions of the present invention can be used as a textile disinfectant/sanitizer.

In other embodiments, the liquid compositions of the present invention can be used as bleaching compositions for a variety of substrates and surfaces, e.g. textiles, hard surfaces.

The liquid compositions of the invention can be used for a variety of domestic or industrial applications, e.g. to reduce microbial or viral populations on a surface or object or in a body or stream of water.

The liquid compositions can be applied in a variety of areas including kitchens, bathrooms, factories, hospitals, dental offices and food plants, pharmaceutical plants and can be applied to a variety of hard or soft surfaces having smooth, irregular or porous topography.

Suitable hard surfaces comprise, for example, architectural surfaces, e.g. floors, walls, windows, sinks, tables, counters and signs; eating utensils; hard-surface medical or surgical instruments and devices; and hard-surface packaging.

Such hard surfaces can be made from a variety of materials including, for example, ceramic, metal, glass, wood or hard plastic.

Suitable soft surfaces comprise, for example paper; filter media; hospital and surgical linens and garments; soft-surface medical or surgical instruments and devices; and soft-surface packaging.

Such soft surfaces can be made from a variety of materials including, for example, paper, fiber, woven or nonwoven fabric, soft plastics and elastomers.

The liquid compositions of the invention can also be applied to soft surfaces such as food and skin, e.g. a hand.

The liquid compositions of the invention can be used as or comprised in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs and rubs.

The liquid compositions can also be used as or in veterinary products such as mammalian skin treatments or in products for sanitizing or disinfecting animal enclosures, pens, watering stations, and veterinary treatment areas such as inspection tables and operation rooms. The liquid compositions can be employed in an antimicrobial foot bath for livestock or people. The compounds of the present invention can also be employed as an antimicrobial teat dip.

In some aspects, the liquid compositions of the present invention can be employed for reducing the population of pathogenic microorganisms, such as pathogens of humans, animals, and the like.

In addition, the present liquid compositions can kill pathogenic microorganisms that spread through transfer by water, air, or a surface substrate. The liquid compositions need only be applied to the skin, other external or mucosal surfaces of an animal water, air, or surface.

The liquid compositions can also be used on foods and plant species to reduce surface microbial populations; used at manufacturing or processing sites handling such foods and plant species; or used to treat process waters around such sites. For example, the liquid compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices.

The liquid compositions of the invention can be used to treat produce transport waters such as those found in flumes, pipe transports, cutters, slicers, blanchers, retort systems, washers, and the like. Particular foodstuffs that can be treated with liquid compositions of the invention comprise eggs, meats, seeds, leaves, fruits and vegetables. Particular plant surfaces comprise both harvested and growing leaves, roots, seeds, skins or shells, stems, stalks, tubers, corms, fruit, and the like. The liquid compositions may also be used to treat animal carcasses to reduce both pathogenic and non-pathogenic microbial levels.

The liquid compositions can also be used to treat waste water where both its antimicrobial function and its oxidant properties can be utilized. Aside from the microbial issues surrounding waste water, it is often rich in malodorous compounds of reduced sulfur, nitrogen or phosphorous. A strong oxidant such as the present invention converts these compounds efficiently to their odor free derivatives e.g. the sulfates, phosphates and amine oxides. These same properties are very useful in the pulp and paper industry where the property of bleaching is also of great utility.

In some aspects, the liquid compositions of the present invention are useful in the cleaning or sanitizing of containers, processing facilities, or equipment in the food service or food processing industries. The liquid compositions have particular value for use on food packaging materials and equipment, and especially for cold or hot aseptic packaging. Examples of process facilities in which the compound of the invention can be employed comprise a milk line dairy, a continuous brewing system, food processing lines such as pumpable food systems and beverage lines, etc.

Food service wares can be disinfected with the liquid compositions of the invention. For example, the compounds can also be used on or in ware wash machines, low temperature ware wash machines, dishware, bottle washers, bottle chillers, warmers, third sink washers, cutting areas, e.g., water knives, slicers, cutters and saws, and egg washers. Particular treatable surfaces comprise packaging such as cartons, bottles, films and resins; dish ware such as glasses, plates, utensils, pots and pans; ware wash and low temperature ware wash machines; exposed food preparation area surfaces such as sinks, counters, tables, floors and walls; processing equipment such as tanks, vats, lines, pumps and hoses, e.g., dairy processing equipment for processing milk, cheese, ice cream and other dairy products; and transportation vehicles. Containers comprise glass bottles, PVC or polyolefin film sacks, cans, polyester, PEN or PET bottles of various volumes (100 ml to 2 liter, etc.), one gallon milk containers, paper board juice or milk containers, etc.

The liquid compositions can also be used on or in other industrial equipment and in other industrial process streams such as heaters, cooling towers, boilers, retort waters, rinse waters, aseptic packaging wash waters, and the like. The liquid compositions can be used to treat microbes and odors in recreational waters such as in pools, spas, recreational flumes and water slides, fountains, and the like.

The liquid compositions of the present invention can also be employed by dipping food processing equipment into the use solution, soaking the equipment for a time sufficient to sanitize the equipment, and wiping or draining excess solution off the equipment.

The liquid compositions may be further employed by spraying or wiping food processing surfaces with the use solution, keeping the surfaces wet for a time sufficient to sanitize the surfaces, and removing excess solution by wiping, draining vertically, vacuuming, etc.

The liquid compositions of the present invention may also be used in a method of sanitizing hard surfaces such as institutional type equipment, utensils, dishes, health care equipment or tools, and other hard surfaces.

The liquid compositions can be applied to microbes or to soiled or cleaned surfaces using a variety of methods.

These methods can operate on an object, surface, in a body or stream of water or a gas, or the like, by contacting the object, surface, body, or stream with a compound of the invention.

Contacting can comprise any of numerous methods for applying a compound, such as spraying the compound, immersing the object in the compound, foam or gel treating the object with the compound, or a combination thereof.

A concentrate or use liquid compositions of the present invention can be applied to or brought into contact with an object by any conventional method or apparatus for applying an antimicrobial or cleaning compound to an object.

For example, the object can be wiped with, sprayed with, foamed on, and/or immersed in the liquid compositions, or use liquid compositions made from the concentrated liquid compositions.

The liquid compositions can be sprayed, foamed, or wiped onto a surface; the compound can be caused to flow over the surface, or the surface can be dipped into the compound.

Contacting can be manual or by machine.

Other hard surface cleaning applications for the liquid compositions of the present invention comprise clean-in-place systems (CIP), clean-out-of-place systems (COP), washer-decontaminators, sterilizers, textile laundry machines, ultra and nanofiltration systems and indoor air filters.

COP systems can comprise readily accessible systems including wash tanks, soaking vessels, mop buckets, holding tanks, scrub sinks, vehicle parts washers, non-continuous batch washers and systems, and the like.

CIP systems comprise the internal components of tanks, lines, pumps and other process equipment used for processing typically liquid product streams such as beverages, milk, and juices.

EXAMPLES

An experiment was performed to determine the bactericidal efficacy of a composition according to the present invention E1 to E12 with a hydrocarbon and without a hydrocarbon C1 to C4.

The test method followed was according to European Standard EN 13704: Quantitative Suspension Test for the Evaluation of Sporicidal Activity of Chemical Disinfectants and Antiseptics Used in Food, Industrial, Domestic and Institutional Areas. Generally, a test suspension of bacterial spores in a solution of interfering substance, simulating clean conditions, was added to a prepared sample of the test formulation diluted in hard water. The mixture was maintained at the specific temperature and time desired. At this contact time, an aliquot is taken; the sporicidal action in this portion was immediately neutralized or suppressed by a validated method. The number of surviving bacterial spores in each sample was determined and the reduction in viable counts was calculated.

with example E2 a minor log reduction at 30 min. and 60 min. contact time are still better log reduction compared to the comparative example C2. Thus, it can be clearly taken from table 1, that the content of hydrocarbon independent from the used alcohol increases the bactericidal efficacy of a composition.

Example E7 corresponds with example E1 with the exception that the composition E7 comprises ethanol instead of 1-propanol. Varying the alcohol from 1-propanol to

TABLE I

| components | | | | | | example no. | | | | | | |
|---|---|---|---|---|---|---|---|---|---|---|---|---|
| (Gew.-%) | | C1 | E1 | C2 | E2 | E3 | E4 | E5 | E6 | E7 | E8 | E9 |
| 1-proanol | | 80 | 80 | 80 | 80 | 80 | 60 | | | | 95 | 40 |
| 2-propanol | | | | | | | | 80 | | | | |
| ethanol | | | | | | | | | 80 | 80 | | |
| H$_2$O$_2$ | | 6 | 6 | 3 | 3 | 6 | 6 | 3 | 6 | 6 | 1 | 1 |
| petrolether 40/60 | | | 1 | | 1 | | | 1 | 2 | 1 | 0.5 | 10 |
| petrolether 50/70 | | | | | | | 1 | | | | | |
| hexane | | | | | | 0.5 | | | | | | |
| pentane | | | | | | 0.5 | | | | | | |
| water | | | | | | up to 100% | | | | | | |
| log reduction | 15 min | 1.0 | 0.5 | <0.5 | <0.5 | <0.5 | 0.8 | <0.5 | 0.8 | <0.5 | <0.5 | <0.5 |
| EN 13704 | 30 min | 0.9 | 2.9 | 0.8 | 1.2 | 1.0 | 1.1 | 0.9 | 1.3 | 1.3 | <0.5 | <0.5 |
| contact time | 60 min | 1.2 | >3.1 | 0.8 | 2.3 | 1.9 | >3.3 | 1.5 | 3.1 | 2.8 | 1.5 | 2.0 |

Example E1 according to the invention, see table I above, shows that a composition comprising 80 wt.-% 1-propanol, 6 wt.-% 0.5 wt. % hexane and 0.5 wt.-% pentane, 1 wt.-% petrolether 40/60 and up to 100 wt.-% water compared with the composition C1 (comparative example) free of a hydrocarbon provides a significant improved log reduction at 30 min. and 60 min. contact time. Thus, the addition of hydrocarbon increases the bactericidal efficacy.

With respect to Example E3 according to the invention a variation of hydrocarbons has been investigated. Example E3 differs from E1 by using 0.5 wt.-% hexane and 0.5 wt.-% pentane instead of petrolether 40/60. It can be taken from table I above that E3 compared with the composition C1 (comparative example) free of a hydrocarbon provides a significant improved log reduction at 30 min. and 60 min. contact time. Thus, the addition of hydrocarbon mixture of hexane and pentane increases the bactericidal efficacy.

Further, the effect of reducing the amount of hydrogen peroxide has been investigated by comparing Example E2 with the comparative composition C2 free of hydrocarbons. Example E2 differs from E1 in that the amount of hydrogen peroxide has been divided by half. Although the hydrogen peroxide concentration has been lowered by half, the composition E2 according to the invention shows compared with C2 (comparative example) an improved log reduction at 30 min. and 60 min. contact time.

Example E4 according to the invention of table I differs from E1 in that the amount of 1-propanol has be reduced from 80 wt.-% to 60.-% wt.-% and instead of petrolether 40/60 a petrolether 50/70 was used to study the effect of reducing the alcohol concentration of the composition. The composition E4 (60 wt.-% 1-propanol) according to the invention compared with C1 (80 wt.-% 1 propanol and free of hydrocarbon) provides an improved log reduction at 30 min. and 60 min. contact time. Thus, E4 clearly shows, see table I, that the use of a hydrocarbon increases the bactericidal efficacy of the composition.

Example E5 of the invention differs from example E2 of table I in that 2-propanol is used instead of 1-propanol. Using 2-propanol instead of 1-propanol provides compared ethanol shows that the composition of E7 compared with C1 provides still a significant log reduction at 30 min. and 60 min. contact time. It can be clearly taken from table 1 again, that the content of hydrocarbon independent from the used alcohol increases the bactericidal efficacy of a composition.

Example E6 of the invention differs from E7 in that the amount of petrolether 40/60 has been doubled from 1 wt.-% to 2 wt.-%. These variations of petrolether 40/60 concentration clearly demonstrate that increasing the content of hydrocarbon has a significant effect of additional improving the log reduction at 30 min. and 60 min. contact time. Therefore, increasing the amount of hydrocarbon increases the bactericidal efficacy of the composition.

In order to demonstrate the effect of hydrocarbon addition to an alcoholic composition with a low 1 wt.-% H$_2$O$_2$ concentration, example E8 and example E9 of table 1 have been tested. The log reduction at 60 min. contact time of E8 and E9 are significant improved compared to the comparative examples C1 and C2. Further, the composition of example E8 is a 95 wt.-% 1-propanol solution and the composition E9 is a 40 wt.-% 1-propanol solution compared to examples C1 and C2 being a 80 wt.-% 1-propanol solution. The evaluation of E8 and E9 with C1 and C2 clearly demonstrate that the improved bactericidal efficacy of E8 and E9 depends on the addition of petrolether.

According to table II below, the effect of varying the amount of hydrogen peroxide up to 10 wt.-% have been investigated.

TABLE II

| | example no. | | | |
|---|---|---|---|---|
| components (% w/w) | E10 | E11 | E12 | C3 |
| 1-proanol | 40 | 80 | 60 | 60 |
| 2-propanol | | | | |
| ethanol | | | | |
| H$_2$O$_2$ | 10 | 4 | 10 | 10 |
| petrolether 40/60 | 10 | 5 | 2 | |
| petrolether 50/70 | | | | |

TABLE II-continued

| components (% w/w) | | E10 | E11 | E12 | C3 |
|---|---|---|---|---|---|
| hexane | | | | | |
| pentane | | | | | |
| water | | up to 100% | | | |
| log reduction | 15 min | 1.5 | 1.1 | 1.8 | <0.5 |
| EN 13704 | 30 min | >3.3 | 2.3 | >3.3 | 1.4 |
| contact time | 60 min | >3.3 | >3.3 | >3.3 | >3.3 |

The comparative example C3 of table II consists of 60 wt.-% 1-propanol, 10 wt.-% hydrogen peroxide and up to 100 wt.-% of water. Comparing example E12 comprising 2 wt.-% of petrolether 40/60 with C3, it can be demonstrated that the addition of a hydrocarbon, such as petrolether 40/60, speeds up the log reduction at 15 min. and at 30 min. contact time. It is surprising that the log reduction at 15 min. and 30 min. for a composition containing already 10 wt.-% hydrogen peroxide can be improved by adding a hydrocarbon.

Example E10 of table II comprises a reduced amount of 40 wt.-% 1-propanol compared with the comparative example C3. Nevertheless, the composition of E10 shows a significant increased log reduction at 15 min. and 30 min. compared to C3 due to the addition of hydrocarbon.

Due to the addition of hydrocarbon, the composition of example E11 according to the invention comprising of 4 wt.-% hydrogen peroxide and of 80 wt.-% 1-propanol also shows an increased log reduction at 15 min. and 30 min. compared to C3.

Tables I and II clearly demonstrate that the addition of a hydrocarbon speeds up and/or enhances the antimicrobial, especially the sporicidal activity, of an alcohol and peroxide containing liquid composition as shown by the examples E1 to E12 according to the invention compared with the comparative examples C1 to C3.

It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims.

In addition, the contents of all patent publications discussed supra are incorporated in their entirety by this reference.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

We claim:

1. A liquid composition comprising:
   a) about 40-95 wt-% of at least one alcohol;
   b) about 1-10 wt-% of at least one hydrocarbon or hydrocarbon mixture;
   c) about 1-10 wt-% of at least one peroxide agent;
   d) water,
   wherein the liquid composition is an antimicrobial, bleaching or disinfectant composition,
   wherein the hydrocarbon or hydrocarbon mixture comprises pentane, hexane, heptane, a petroleum ether, or a combination thereof, is an active ingredient of the composition, not a propellant and has a boiling point in the range of about 40° C. to about 80° C.,
   wherein the at least one alcohol is a $C_2$-$C_6$ alcohol, and
   wherein the peroxide agent comprises hydrogen peroxide, a peroxycarboxylic acid, a derivative thereof, or a mixture thereof.

2. The composition of claim 1, wherein the ratio of the at least one alcohol to the at least one hydrocarbon or hydrocarbon mixture is in the range of about 5: 1 to 100 : 0.1.

3. The composition of claim 1, wherein the hydrocarbon is a hydrocarbon mixture.

4. The composition of claim 1, wherein the hydrocarbon or hydrocarbon mixture has a boiling point in the range of about 30° C. to about 40° C.

5. The composition of claim 1, wherein the alcohol comprises ethanol, 1-propanol, 2-propanol, n-butan-1-ol, n-butan-2-ol, tert-butanol, pentan-1-ol, pentan-2-ol, pentan-3-ol, 3-methylbutan-2-ol, 2,2-dimethylpropanol, hexan-1-ol, hexan-2-ol, hexan-3-ol, an isomer thereof, or a combination thereof.

6. The composition of claim 1, wherein the composition has about 1-5 wt-% of the at least one hydrocarbon.

7. The composition of claim 1, wherein the composition has about 60-80 wt-% of the at least one alcohol.

8. The composition of claim 1, wherein the composition has about 3-8 wt-% of the at least one peroxide agent.

9. The composition of claim 1, wherein the composition has about 40-95 wt-% of the at least one alcohol;
   about 1-10 wt-% of the at least one hydrocarbon; and
   about 1-10 wt-% of the at least one peroxide agent
      wherein the at least one alcohol is a $C_2$-$C_6$ alcohol and the at least one hydrocarbon has a boiling point of about 40-60° C.,
   wherein the hydrocarbon comprises pentane, hexane, heptane, a petroleum ether, or a combination thereof.

10. The composition of claim 1, wherein the composition has a pH of about 1-10.

11. A method for disinfection or cleaning of a hard surface or a soft surface comprising contacting a hard or soft surface with an effective amount of the composition according to claim 1.

12. The composition of claim 1, wherein the composition has an antimicrobial or microbiocidal activity.

13. The composition of claim 9, wherein the composition has an antimicrobial or microbiocidal activity.

14. The composition of claim 1, wherein the composition is a bleaching composition.

15. The composition of claim 7, wherein the $C_2$-$C_6$ alcohol comprises propanol.

16. The method of claim 11, wherein the surface comprises a surface of a medical or dental instrument, a surface of a medical or dental device, a surface of a pharmaceutical equipment, or a surface of a pharmaceutical or cosmetics manufacturing equipment.

* * * * *